United States Patent
Biedermann et al.

(10) Patent No.: US 9,023,086 B2
(45) Date of Patent: May 5, 2015

(54) RECEIVING PART FOR RECEIVING A ROD FOR COUPLING THE ROD TO A BONE ANCHORING ELEMENT AND A BONE ANCHORING DEVICE WITH SUCH A RECEIVING PART

(71) Applicant: Biedermann Technologies GmbH & Co. KG, Donaueschingen (DE)

(72) Inventors: Lutz Biedermann, VS-Villingen (DE); Wilfried Matthis, Weisweil (DE); Berthold Dannecker, St. Georgen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/942,418

(22) Filed: Jul. 15, 2013

(65) Prior Publication Data
US 2014/0018859 A1     Jan. 16, 2014

Related U.S. Application Data

(63) Continuation of application No. 12/649,194, filed on Dec. 29, 2009, now Pat. No. 8,506,609.

(60) Provisional application No. 61/141,512, filed on Dec. 30, 2008.

(30) Foreign Application Priority Data

Dec. 30, 2008   (EP) ..................................... 08022553

(51) Int. Cl.
*A61B 17/04*   (2006.01)
*A61B 17/86*   (2006.01)
(Continued)

(52) U.S. Cl.
CPC ......... *A61B 17/7032* (2013.01); *A61B 17/7037* (2013.01); *A61B 17/7002* (2013.01)

(58) Field of Classification Search
USPC .................................. 606/265–270, 305–308
See application file for complete search history.

(56) References Cited

U.S. PATENT DOCUMENTS

| 5,578,033 A | 11/1996 | Errico et al. |
| 5,584,834 A | 12/1996 | Errico et al. |

(Continued)

FOREIGN PATENT DOCUMENTS

| EP | 0 836 835 A2 | 4/1998 |
| EP | 1 749 489 A1 | 2/2007 |

(Continued)

OTHER PUBLICATIONS

European Search Report for European Application 08022553.5 in the name of Biedermann Motech GmbH, European Search Report dated May 18, 2009 and mailed May 28, 2009 (7 pgs.).

(Continued)

*Primary Examiner* — Andrew Yang
(74) *Attorney, Agent, or Firm* — Christie, Parker & Hale, LLP

(57) ABSTRACT

A receiving part for coupling a rod to a bone anchoring element includes a receiving part body including a rod receiving portion having a channel for receiving a rod, and a head receiving portion for accommodating a head of a bone anchoring element, the head receiving portion having an open end and being flexible for inserting and clamping of the head; and a locking ring around the head receiving portion, wherein in a pre-locking position, a spring portion on one of the locking ring or the receiving part body engages a corresponding portion on the other one of the locking ring or the receiving part body, and the locking ring exerts a first force onto the head receiving portion, and wherein in a locking position, the locking ring exerts a second force greater than the first force onto the head receiving portion to lock the head therein.

22 Claims, 9 Drawing Sheets

(51) Int. Cl.
 *A61F 2/08* (2006.01)
 *A61B 17/70* (2006.01)

(56) References Cited

U.S. PATENT DOCUMENTS

| | | | |
|---|---|---|---|
| 5,586,984 | A | 12/1996 | Errico et al. |
| 5,609,593 | A | 3/1997 | Errico et al. |
| 5,672,176 | A | 9/1997 | Biedermann et al. |
| 5,728,098 | A | 3/1998 | Sherman et al. |
| 6,010,503 | A | 1/2000 | Richelsoph et al. |
| 6,254,602 | B1 | 7/2001 | Justis |
| 6,355,040 | B1 | 3/2002 | Richelsoph et al. |
| 6,454,773 | B1 | 9/2002 | Sherman et al. |
| 6,582,436 | B2 | 6/2003 | Schlapfer et al. |
| 7,090,674 | B2 | 8/2006 | Doubler et al. |
| 7,585,315 | B2 | 9/2009 | Donath |
| 7,682,377 | B2 | 3/2010 | Konieczynski et al. |
| 2001/0047173 | A1 | 11/2001 | Schlapfer et al. |
| 2002/0032443 | A1 | 3/2002 | Sherman et al. |
| 2003/0100896 | A1 | 5/2003 | Biedermann et al. |
| 2003/0100904 | A1 | 5/2003 | Biedermann |
| 2003/0187439 | A1 | 10/2003 | Biedermann et al. |
| 2005/0080415 | A1 | 4/2005 | Keyer et al. |
| 2005/0096653 | A1 | 5/2005 | Doubler et al. |
| 2006/0161153 | A1 | 7/2006 | Hawkes et al. |
| 2006/0200128 | A1 | 9/2006 | Mueller |
| 2007/0055241 | A1 | 3/2007 | Matthis et al. |
| 2007/0093817 | A1 | 4/2007 | Barrus et al. |
| 2008/0015576 | A1 | 1/2008 | Whipple |
| 2008/0027432 | A1 | 1/2008 | Strauss et al. |
| 2008/0108992 | A1 | 5/2008 | Barry et al. |
| 2008/0119857 | A1 | 5/2008 | Potash et al. |
| 2008/0161859 | A1 | 7/2008 | Nilsson |
| 2008/0183216 | A1 | 7/2008 | Jackson |
| 2008/0243193 | A1 | 10/2008 | Ensign et al. |
| 2009/0036934 | A1 | 2/2009 | Biedermann et al. |
| 2009/0062867 | A1 | 3/2009 | Schumacher |
| 2009/0105716 | A1 | 4/2009 | Barrus |
| 2009/0105756 | A1 | 4/2009 | Richelsoph |
| 2009/0105769 | A1 | 4/2009 | Rock et al. |
| 2009/0105770 | A1 | 4/2009 | Berrevoets et al. |
| 2009/0143827 | A1 | 6/2009 | Levy et al. |
| 2009/0149887 | A1 | 6/2009 | Schlaepfer et al. |

FOREIGN PATENT DOCUMENTS

| | | |
|---|---|---|
| EP | 2 022 423 A1 | 2/2009 |
| KR | 2003-0043722 A | 6/2003 |
| KR | 2003-0043723 A | 6/2003 |
| KR | 2003-0078008 A | 10/2003 |
| KR | 10-2007-0008391 | 1/2007 |
| WO | WO 2007/038350 A2 | 4/2007 |
| WO | WO 2007/038351 A3 | 4/2007 |
| WO | WO 2007/075454 A1 | 7/2007 |

OTHER PUBLICATIONS

Non-final Office action for U.S. Appl. No. 13/101,989, dated Jan. 31, 2013 (26 pgs.).

Notice of Allowance for Application No. KR 10-2009-0130950, dated Mar. 3, 2015 and English translation, 7 pages.

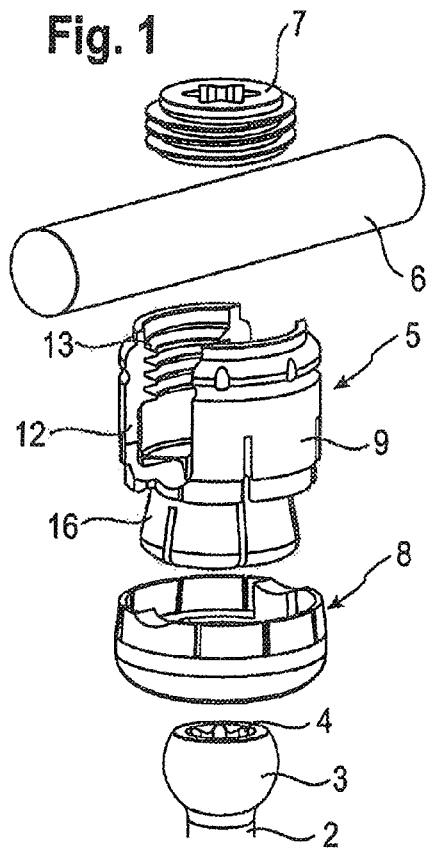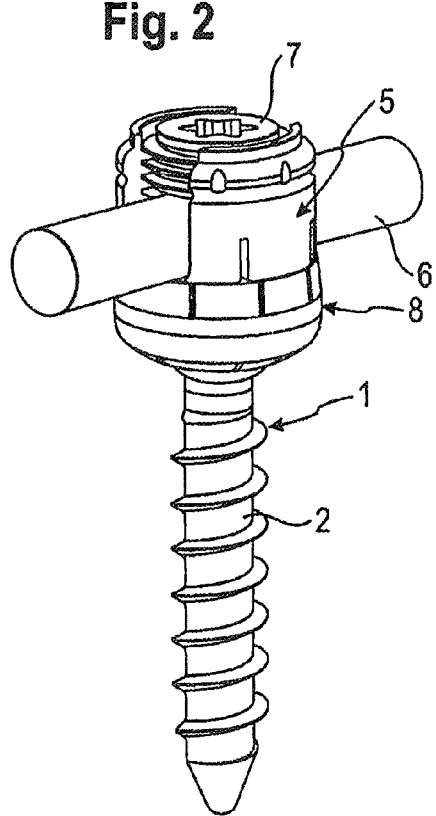

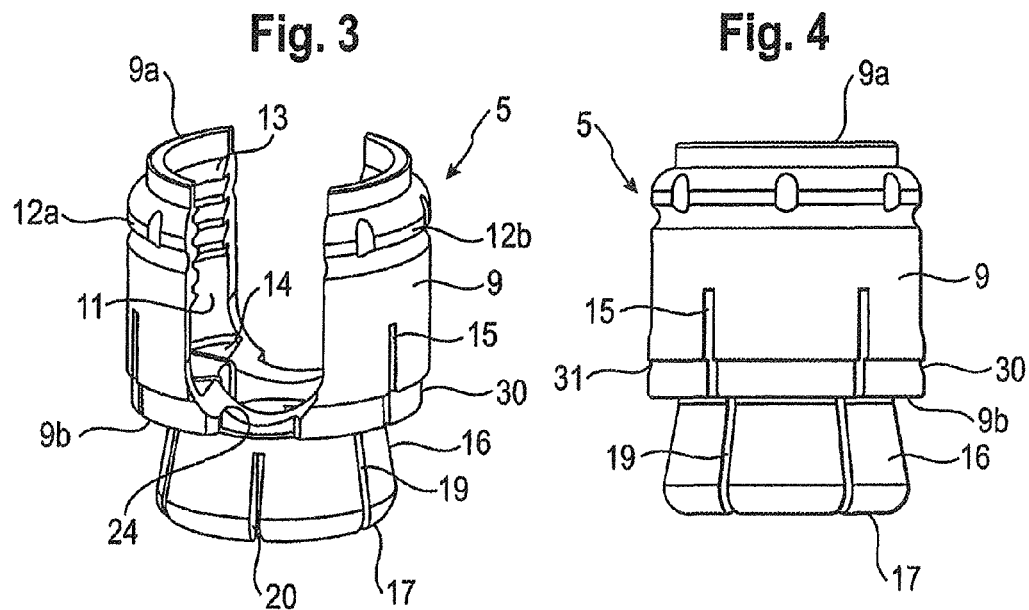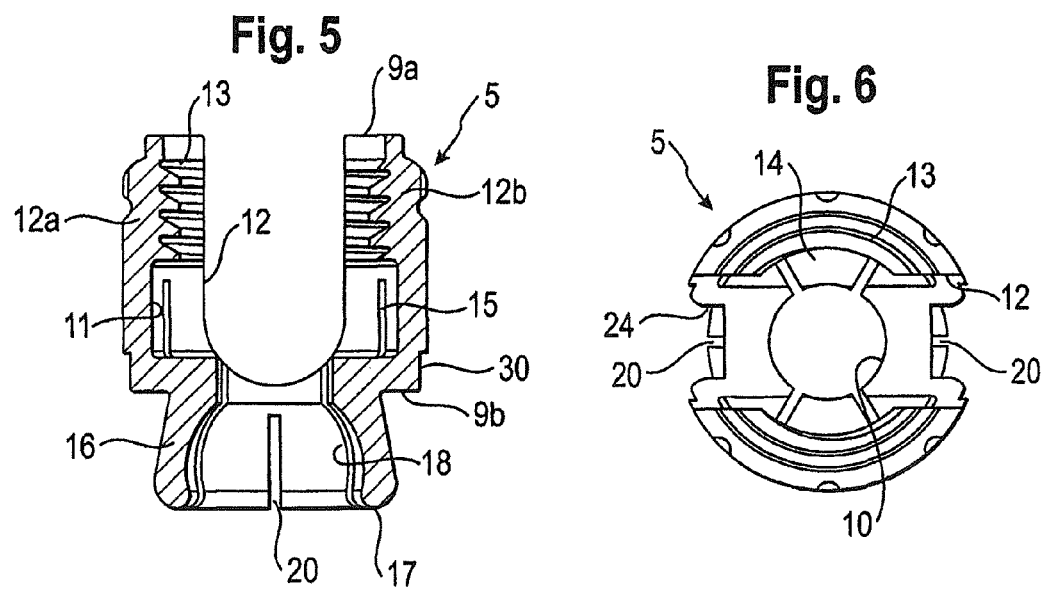

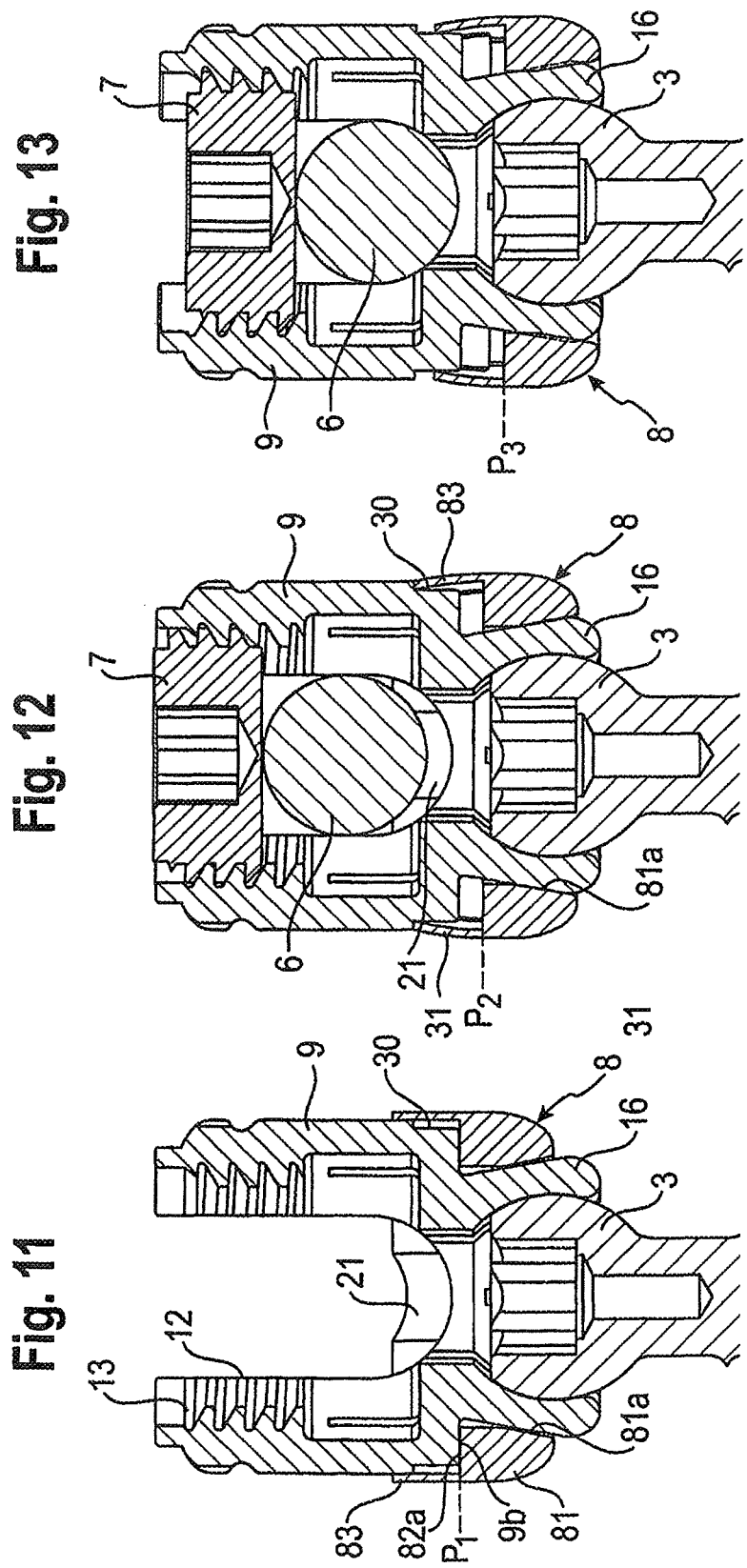

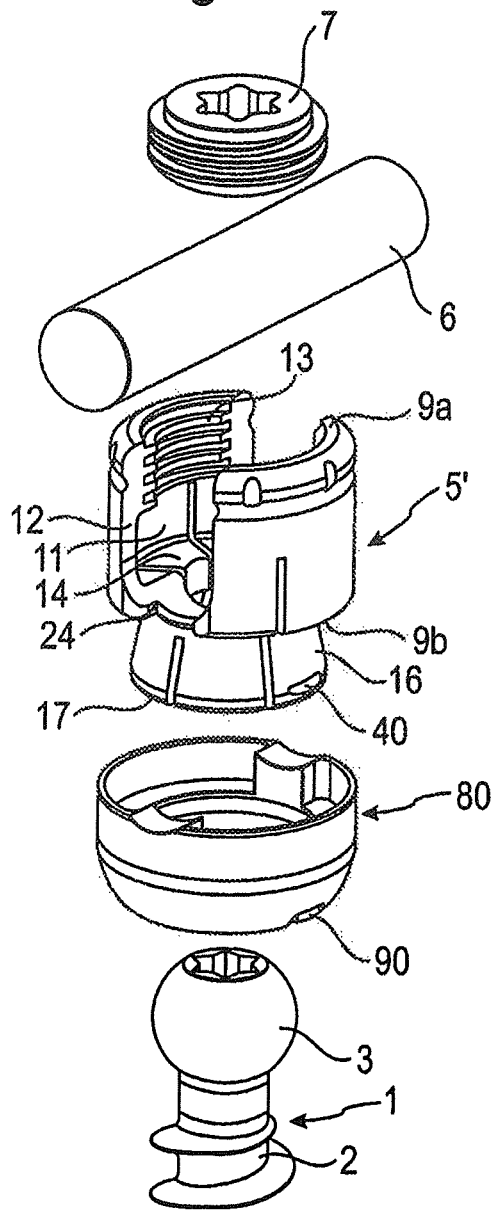
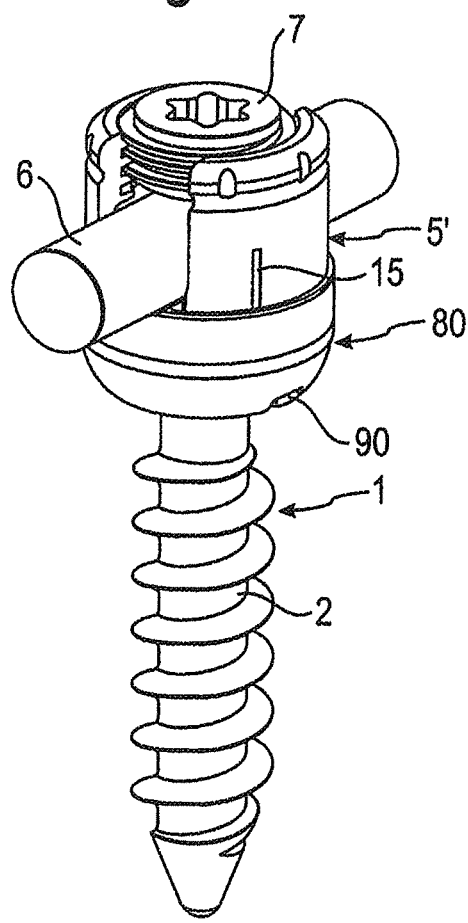

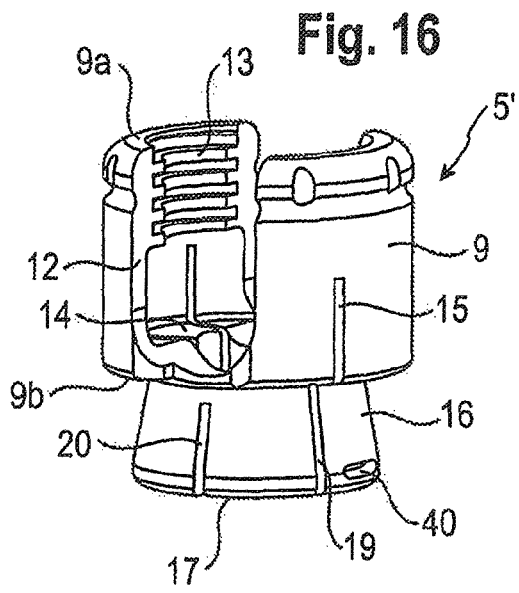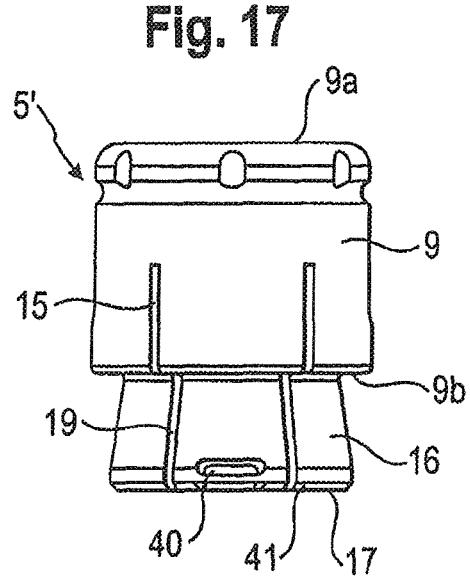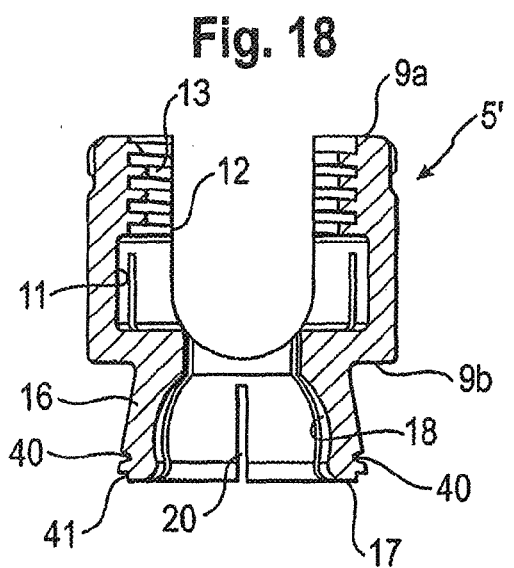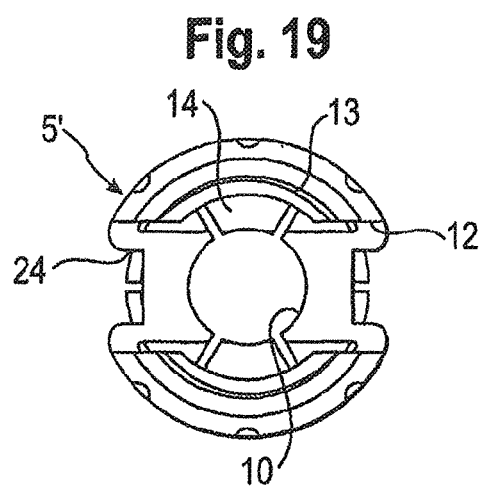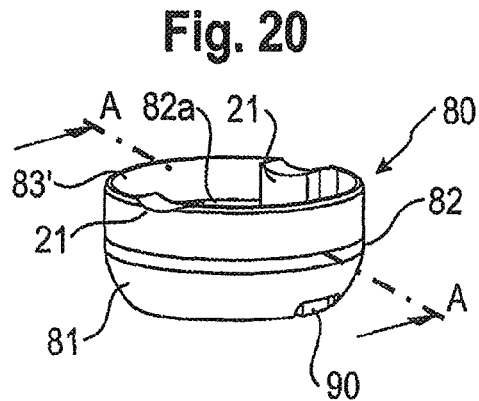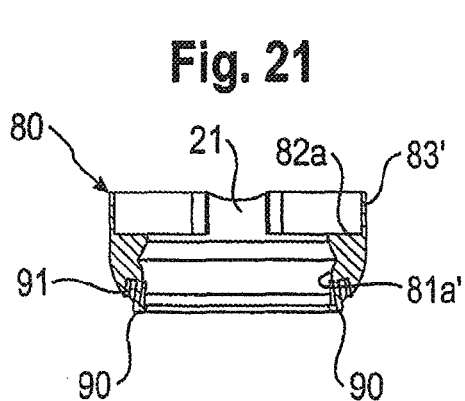

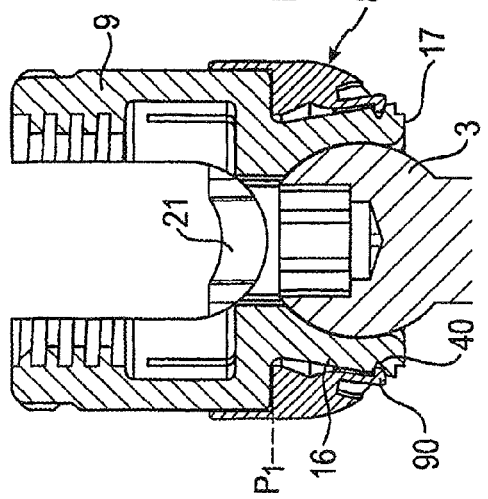
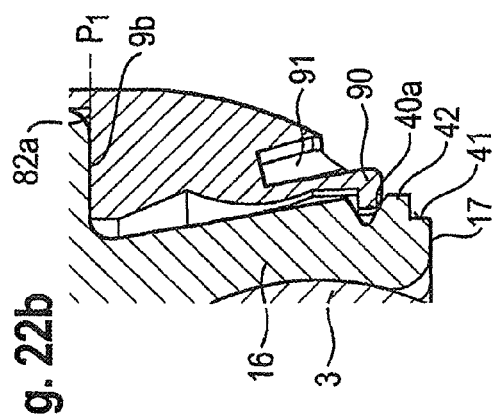
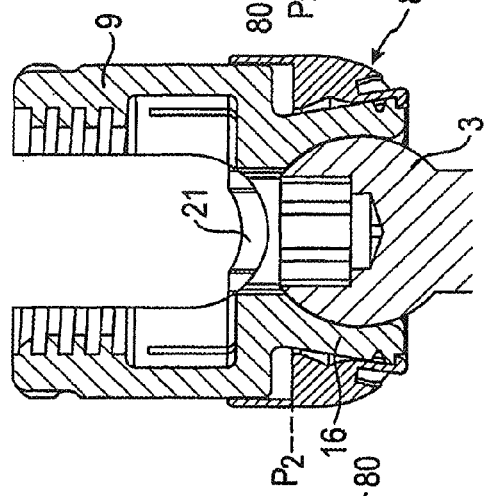
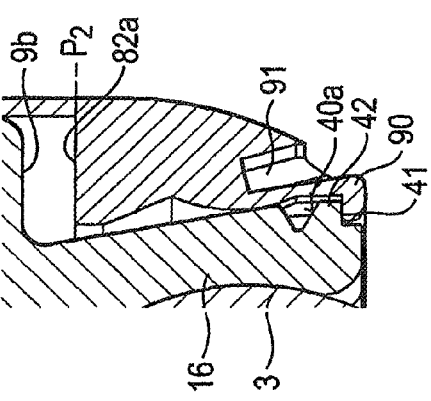
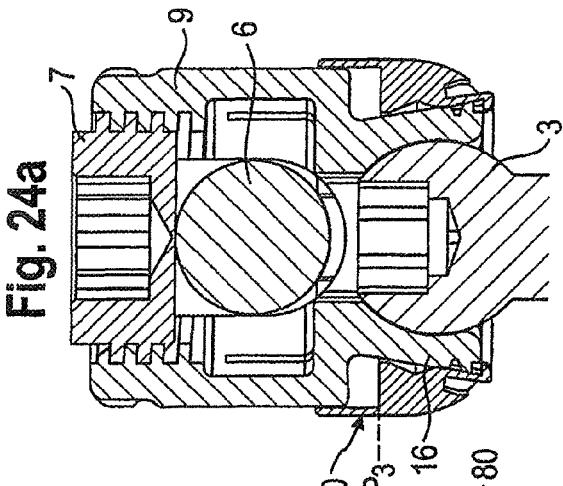
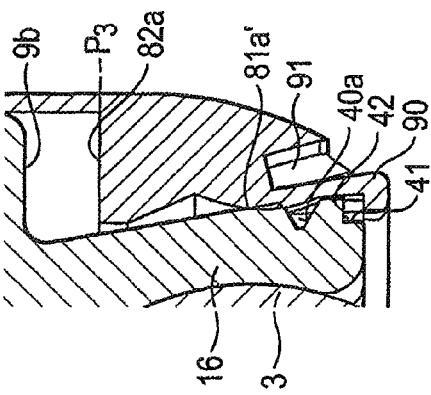

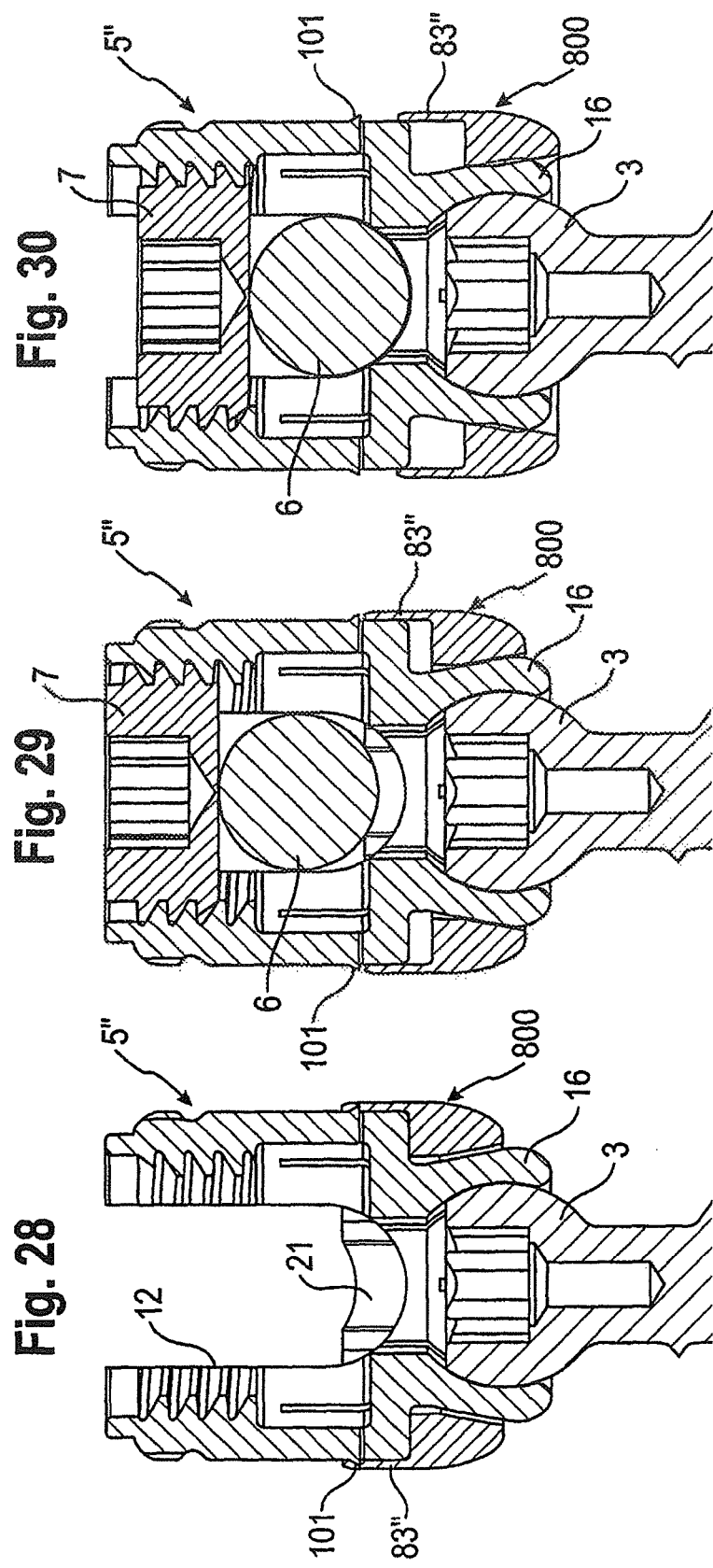

RECEIVING PART FOR RECEIVING A ROD FOR COUPLING THE ROD TO A BONE ANCHORING ELEMENT AND A BONE ANCHORING DEVICE WITH SUCH A RECEIVING PART

CROSS-REFERENCE TO RELATED APPLICATION(S)

This application is a continuation of U.S. patent application Ser. No. 12/649,194, filed Dec. 29, 2009, which claims the benefit of U.S. Provisional Patent Application Ser. No. 61/141,512, filed Dec. 30, 2008, the contents of which are hereby incorporated by reference in their entirety, and claims priority from European Patent Application EP 08 022 553.5, filed Dec. 30, 2008, the contents of which are hereby incorporated by reference in their entirety.

BACKGROUND

1. Field of the Invention

The invention relates to a receiving part for receiving a rod for coupling the rod to a bone anchoring element and a bone anchoring device with such a receiving part. The receiving part includes a receiving part body and a locking ring. The head of the bone anchoring element is locked in the receiving part body by compression of a head receiving portion of the receiving part laterally surrounding the head by means of the locking ring. The bone anchoring device can be realized, for example, in the form of a polyaxial bone screw.

2. Description of Related Art

Various designs of polyaxial bone screws wherein the head is clamped from the side to lock the rotational position of the bone screw are known.

U.S. Pat. No. 5,672,176 describes a bone screw with a receiving part with a conically shaped seat and a conically shaped pressure element which exerts pressure onto the head from above and from the side. If the cone angle has a value laying within a specific range self-locking of the pressure element within the receiving part takes place which allows to preliminary lock the head within the receiving part while the rod is still movable in order to allow the adjustment of its position.

U.S. Pat. No. 5,728,098 describes a bone screw for connection to a spinal rod comprising a screw element and a receiver member which has slits provided at the bottom of the rod receiving channel and wherein two ring-shaped compression members made of a shaped-memory alloy are provided at the lower side and the upper side of the receiver member, respectively. The compression members contract about the portions of the receiver member when the temperature is elevated so that the rod is clamped in the channel.

WO 2007/038350 A2 discloses an apparatus for connecting a bone anchor to a support rod, the apparatus including a connector body and a cap. The connector body has a socket for insertion, angulation and removal of a bone anchor. A sleeve is provided which is configured to fit over the connector body in a temporary position in which the sleeve permits insertion of the bone anchor, to move to a provisional locking position in which the sleeve permits angulation but prevents removal of the bone anchor, and to move to a locking position in which the sleeve prevents both angulation and removal of the bone anchor. The sleeve extends over the whole length of the socket.

SUMMARY

It is the object of the invention to provide an improved receiving part for receiving a rod for coupling the rod to a bone anchoring element and a bone anchoring device with such a receiving part which has a small size while simultaneously providing for safer handling during surgery and a safer and more secure final locking.

A locking ring can be arranged in three positions. In an insertion position, the head is insertable into the head receiving portion. In a pre-locking position, the locking ring pre-locks the head in the head receiving portion which prevents inadvertent removal of the head from the receiving part body, and prevents inadvertent movement of the head with respect to the receiving part body during surgery. This allows for safer handling of the bone anchoring device during surgery. In a locking position, the head is locked in the receiving part. The locking ring can be releasably held in the insertion position and in the pre-locking position. This makes handling more convenient.

Pre-locking and final locking of the head are achieved with a single locking ring. Hence, the receiving part and the bone anchoring device according to embodiments of the invention comprise fewer elements, which reduces the costs of manufacturing and which facilitates handling. It makes use of the principle of clamping the head of the bone anchoring element circumferentially from the lateral sides which reduces the force necessary to safely clamp the head. The design of the receiving part allows to further reduce the dimension in terms of height as well as in terms of the bottom outer diameter which is particularly suitable for applications where small-sized anchoring devices are utilized, such as in the field of cervical spinal surgery or paediatric applications, trauma and minimally invasive applications.

By providing various bone anchors with different receiving parts a modular system is available prior to surgery.

The receiving part can be designed with a small diameter. The pressure exerted via the locking ring onto the head receiving portion is largest at a position of the largest diameter of the head of the bone anchoring element. Therefore, the locking ring does not have to extend up to the open end of the head receiving portion which allows for a locking ring with a reduced diameter at the bottom end.

When the locking ring has a curved interior surface portion, jamming between the locking ring and the head receiving portion does not occur.

BRIEF DESCRIPTION OF THE DRAWINGS

Further features and advantages of the invention will become apparent from the description of embodiments using the accompanying drawings. In the drawings:

FIG. 1 shows a perspective exploded view of a first embodiment of the bone anchoring device.

FIG. 2 shows a perspective view of the bone anchoring device of FIG. 1 in an assembled state.

FIG. 3 shows a perspective view of the receiving part body according to the first embodiment.

FIG. 4 shows a side view of the receiving part body of FIG. 3.

FIG. 5 shows a cross-sectional view of the receiving part body FIG. 3, the section being taken perpendicular to the rod axis.

FIG. 6 shows a top view of the receiving part body of FIG. 3.

FIG. 11 shows a cross-sectional view of the bone anchoring device of the first embodiment in a first position, the section being taken perpendicular to the rod axis.

FIG. 12 shows a cross-sectional view of the bone anchoring device of FIG. 11 in a second position.

FIG. 13 shows a cross-sectional view of the bone anchoring device of FIG. 11 in a third position.

FIG. 14 shows a perspective exploded view of a second embodiment of the bone anchoring device.

FIG. 15 shows a perspective view of the bone anchoring device of FIG. 14 in an assembled state.

FIG. 16 shows a perspective view of the receiving part body according to the second embodiment.

FIG. 17 shows a side view of the receiving part body of FIG. 16.

FIG. 18 shows a cross-sectional view of the receiving part body FIG. 16, the section being taken perpendicular to the rod axis.

FIG. 19 shows a top view of the receiving part body of FIG. 16.

FIG. 20 shows a perspective view of the locking ring of the second embodiment.

FIG. 21 shows a cross-sectional view of the locking ring of FIG. 20 the section being taken along line A-A in FIG. 20.

FIG. 22a shows a cross-sectional view of the bone anchoring device of the second embodiment in a first position, the section being taken perpendicular to the rod axis.

FIG. 22b shows an enlarged view of a detail of FIG. 22a.

FIG. 23a shows a cross-sectional view of the bone anchoring device of FIG. 22a in a second position.

FIG. 23b shows an enlarged view of a detail of FIG. 23a.

FIG. 24a shows a cross-sectional view of the bone anchoring device of FIG. 22a in a third position.

FIG. 24b shows an enlarged view of a detail of FIG. 24a.

FIG. 28 shows a cross-sectional view of the bone anchoring device of the third embodiment in a first position, the section being taken perpendicular to the rod axis.

FIG. 29 shows a cross-sectional view of the bone anchoring device of FIG. 28 in a second position.

FIG. 30 shows a cross-sectional view of the bone anchoring device of FIG. 28 in a third position.

DETAILED DESCRIPTION

Figure 7:
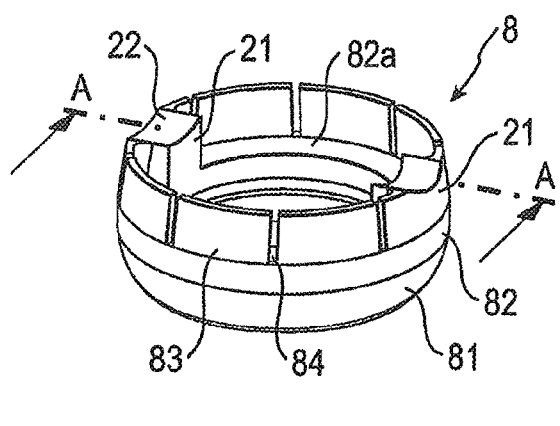
FIG. 7 shows a perspective view of the locking ring of the first embodiment.

As shown in FIGS. 1 and 2, the bone anchoring device according to a first embodiment comprises a bone anchoring element 1 in the form of a bone screw having a threaded shaft 2 and a head 3 with a curved surface portion, in this embodiment a spherical segment-shaped head. The head 3 has a recess 4 for engagement with a screwing-in tool. The bone anchoring device further comprises a receiving part body 5 for receiving a rod to connect it to the bone anchoring element 1. Further, a closure element 7 in the form of an inner screw is provided for securing the rod 6 in the receiving part body 5. In addition, the bone anchoring device includes a locking ring 8 for locking the head in the receiving part body 5.

As can be seen in particular in FIGS. 3 to 6, the receiving part body 5 comprises a rod receiving portion 9 which is substantially cylindrical and which has a first end 9a and a second end 9b opposite the first end 9a. The rod receiving portion 9 has a coaxial first bore 10 provided at the second end 9b. The diameter of the first bore 10 is smaller than the diameter of the head 3 of the bone anchoring element. The rod receiving portion 9 also comprises a coaxial second bore 11 extending from the first end 9a to a distance from the second end 9b. The diameter of the second bore 11 is larger than that of the first bore 10 and larger than the diameter of the rod 6. A substantially U-shaped recess 12 is provided in the rod receiving portion 9 which extends from the first end 9a towards the second end 9b, the diameter of the recess 12 being slightly larger than the diameter of the rod 6 in such a way that the rod 6 can be placed in the recess and can be guided therein. The recess 12 forms two free legs 12a, 12b, on which an internal thread 13 is provided. The internal thread can be a metric thread, a flat thread, a negative angle thread, a saw-tooth thread, or any other thread type. Preferably, a thread form such as a flat thread or negative angle thread is used which prevents or reduces splaying of the legs 12a, 12b when the inner screw 7 is screwed-in. The depth of the recess 12 is such that the rod 6 and the inner screw 7 can be inserted between the legs 12a, 12b. Between the bottom of the recess and the legs 12a, 12b a flat section 14 is provided forming the end of the bore 11.

As can be seen in FIGS. 1, 2, 3 and 6, cuts 24 are provided in the rod receiving portion on either end of the channel formed by the recess 12.

The rod receiving portion 9 of the receiving part body 5 further comprises a plurality of coaxial slits 15 extending from the second end 9b to a distance from the first end 9a, wherein the distance corresponds approximately to the length of the internal thread 13. The slits 15 are open at the second end 9b and extend, as can be seen in particular in FIGS. 1, 3 and 6 through the flat section 14 in the substantially U-shaped recess 12. At least one slit 15, and preferably more than one slit, is provided on either side of the recess 12. The number of slits is provided according to the degree of flexibility which is to be provided by the slits. It may depend, for example, on the material and wall thickness and/or other factors.

In one embodiment, the rod receiving portion has adjacent to its second end 9b an annular recess 30 by which a shoulder 31 is formed at a distance from the second end. The depth of the recess 30 is such that it can cooperate with a portion of the locking ring 8 described below.

Adjacent to the second end 9b the receiving part body 5 comprises a head receiving portion 16 providing an accommodation space for the head 3 of the bone anchoring element 5. The head receiving portion 16 has an outer surface which tapers towards the second end 9b and which has an open end 17 opposite to the second end 9b. The exterior surface of the head receiving portion 16 can be partly or fully tapered. It is tapered at least in the region of the largest diameter of the head 3. The open end 17 can have a rounded edge.

As can be seen in particular in FIGS. 3 to 5, the outer diameter of the rod receiving portion 9 at the second end 9b is larger than the outer diameter of the head receiving portion 16 adjacent to the second end 9b and is also larger than the outer diameter of the head receiving portion at the open end 17. Hence, the head receiving portion 16 is recessed with respect to the rod receiving portion 9.

As can be seen in particular in FIG. 5, the head receiving portion 16 has an internal hollow section 18 forming a seat for the head 3 of the bone anchoring element 1. The hollow section 18 is adapted in its shape to correspond to the shape of the head 3, in the embodiment shown it is a spherical section to accommodate the spherical head 3. The hollow section 18 is dimensioned in such a way that it encompasses the head 3 of the bone anchoring element from the side, covering a region including the largest diameter of the head 3.

A plurality of slits 19 are provided in the head receiving portion 16 which are open to the open end 17 and extend from the open end 17 to the second end 9b of the rod receiving portion, in which all or some may be formed continuously with the slits 15 of the rod receiving portion 9, thereby forming continuous slits extending from the open end 17 of the head receiving portion into the rod receiving portion 9. The number of slits 19 may be equal to the number of slits 15, however, the number of slits can be smaller or larger depending on the desired flexibility of the head receiving portion 16. In addition, slits 20 may be provided on the side of the head receiving portion 16 which is adjacent to the substantially U-shaped recess 12 of the rod receiving portion, as shown in FIG. 6. The slits 20 end at a distance from the second end 9b. The flexibility of the head receiving portion 16 is such that the head 3 of the anchoring element can be inserted by expanding the head receiving portion 16 and can be clamped by compressing the head receiving portion. The slits 15 in the rod receiving portion facilitate mounting of the receiving part body 5 onto the head 3 manually.

Figure 8:
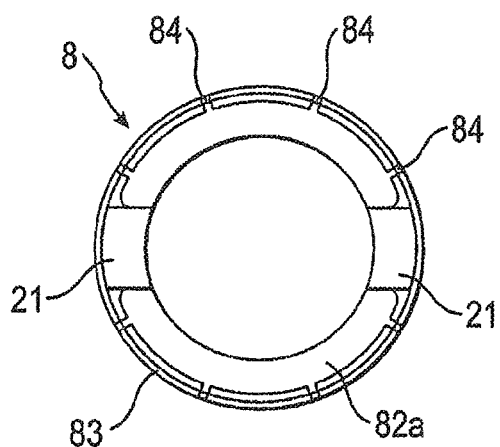
FIG. 8 shows a top view of the locking ring of to FIG. 7.
Figure 9:
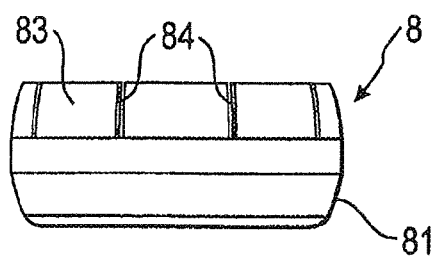
FIG. 9 shows a side view of the locking ring of FIG. 7.
Figure 10:
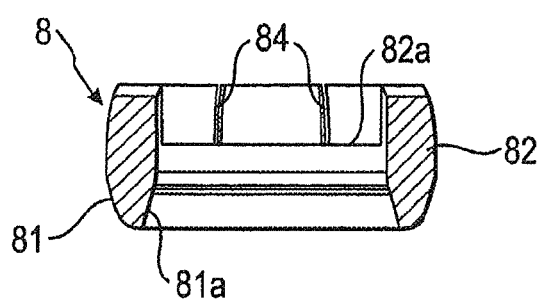
FIG. 10 shows a cross-sectional view of the locking ring of FIG. 7, the section being taken along line A-A in FIG. 7.

The locking ring 8 will now be described with reference to FIGS. 1, 2 and 7 to 13. The locking ring 8 is substantially cylindrical and has a first portion 81 with a tapered inner surface 81a. The outer surface of the first portion may also be tapered to reduce the outer bottom diameter. The size of the first portion 81 is such that the tapered inner surface 81a can engage the tapered portion of the outer surface of the head receiving portion 16 to exert a compression force onto the head receiving portion 16. The inner surface 81a of the first portion can also be curved with a curvature directing to the center of the locking ring.

Further, the locking ring has a cylindrical second portion 82, a free end of which forms an annular surface 82a which can abut against the second end 9b of the rod receiving portion, as shown in FIG. 11.

Two projections 21 which are located diametrically opposite to each other extend from the annular surface 82a in the direction of the second end 9b of the rod receiving portion. The projections 21 have a height such that they project above the bottom of the substantially U-shaped recess 12 and extend into the cuts 24 when the locking ring 8 is in a position in which the head 3 is not yet locked, as shown in FIGS. 11 and 12. The free ends 22 of the projections 21 can be curved, particularly inwardly curved, with a curvature corresponding to that of the rod 6. The locking ring is arranged in such a way around the head receiving portion 16 of the receiving part body 5 that the projections 21 are located at the positions of the recess 12. By means of this, the projections 21 which project into the recess 12 prevent the locking ring from rotating when the rod is not inserted.

A third portion 83 of the locking ring is formed by a slightly tapered annular rim projecting from the outer edge of the annular surface 82. A plurality of coaxial slits 84 may be provided in the rim which are open to the free end and which render the rim radially flexible to some extent. The height of the rim is as shown in FIG. 11, larger than the height of the recess 30 of the rod receiving portion 9. The inner diameter of the rim is such that, as shown in FIG. 11, the locking ring can clamp the rod receiving portion 9 and is held by the pre-stress generated by the flexible rim.

The flexibility of the head receiving portion 16 and the size of the head receiving portion at the open end 17 allows mounting of the locking ring 8 by assembling it from the free end 17 onto the head receiving portion 16. Since the outer diameter of the head receiving portion is smaller than that of the rod receiving portion 9, the locking ring may only project minimally beyond the rod receiving portion in a radial direction.

The inner screw 7 has a thread corresponding to the internal thread 13 provided on the legs. If a thread form which prevents the legs from splaying is used, a single closure element such as the inner screw 7 is sufficient. This reduces the size of the bone anchoring device in a radial direction. Other closure elements such as, for example, an outer nut, are also possible.

The receiving part body 5, the locking ring 8, the inner screw 7 and the bone anchoring element 1 are made of a bio-compatible material, for example, of titanium or a stainless steel or bio-compatible alloy or bio-compatible plastic material with sufficient strength.

The bone anchoring device may be preassembled with the locking ring 8 mounted on the head receiving portion 16 of the receiving part body 5 and with the screw head 3 inserted.

The function of the locking ring is now explained with respect to FIGS. 11 to 13. As shown in FIG. 11, a first position $P_1$ of the locking ring 8 is defined in such a way that the locking ring is in its uppermost position where the annular surface 82a of the locking ring 8 abuts against the second end 9b of the rod receiving portion 9. In this position, the locking ring 8 is held by the pre-stress exerted by the flexible rim 83 onto the rod receiving portion 9. The head receiving portion 16 is not compressed. In this position, the introduction of the screw head 3 is possible.

A second position $P_2$ is the pre-locking position as shown in FIG. 12. In the position $P_2$, the locking ring has been shifted downwards until the flexible rim 83 resiliently snaps into the recess 30 provided on the rod receiving portion 9 and its upper edge abuts against the shoulder 31 of the recess. Since the rim 83 is slightly tapered, the locking ring is held in this position by the pre-stress exerted by the flexible rim 83. The tapered inner surface 81a of the locking ring exerts a pre-stress onto the head receiving portion 16 which pre-locks the head 3. Pre-locking means that under conditions arising during surgery the angular position of the bone anchoring element 1 with respect to the receiving part body 5 is maintained in a temporary position and can be loosened only by exerting an additional force onto the receiving part body or the bone anchoring element. Hence, an inadvertent removal of the head is not possible. The pre-locking position of the locking ring 8 can be achieved either manually by pushing down the locking ring or by inserting the rod and screwing-in the inner screw so that the rod presses onto the projections 21.

A third position $P_3$, which is the locking position, is shown in FIG. 13. The locking position is defined as the position in which the screw head 3 is locked within the head receiving portion. In the position $P_3$ the tapered inner surface 81a engages the outer surface of the head receiving portion 16 in such a way that the head 3 is locked by compression of the head receiving portion. It is achieved by tightening the inner screw 7, thereby pressing down the rod 6. Here, a further downward movement of the locking ring 8 may be prevented.

In some embodiments, the recess 30 in the receiving part body can be omitted. It is also possible that the rim 83 cooperates with the second end 9b of the receiving part body.

In use, the preassembled bone anchoring device comprising the receiving part body, the bone anchoring element, and the locking ring is screwed into the bone. The recess 4 of the head can be accessed with the screw tool through the first bore 10. The locking ring 8 can already be in the pre-locking position $P_2$. To correctly align the receiving part with respect to the rod to which it shall be connected, an additional force is exerted onto the receiving part either manually or by application of an instrument. Once the correct position of the rod with respect to other bone anchoring devices is achieved, the inner screw 7 is tightened thereby shifting down the locking ring 8 into the locking position $P_3$. When the locking ring 8 is moved towards the free end 17 of the head receiving portion, it compresses the head receiving portion, thereby locking the head. Final tightening of the inner screw locks the rod and the head simultaneously.

The bone anchoring device can be preassembled either by the manufacturer or in the course of preparation of the surgery or at any other time. Advantageously, the surgeon selects prior to surgery the necessary receiving parts and bone anchoring elements according to the specific requirements of the clinical application. The design of the bone anchoring device allows selection of the appropriate bone anchoring elements in terms of diameter, length and other features of the anchoring section. Hence, a modular system is provided which may include various receiving parts and several bone anchoring elements, which then individually can be chosen and adapted.

In the pre-locking position the head remains clamped when the inner screw is loosened. This allows for further adjustments of the rod.

A second embodiment of the bone-anchoring device is now described with respect to FIGS. 14 to 24. Parts which are similar to those of the first embodiment have the same reference numerals and the descriptions thereof will not be repeated. The second embodiment of the bone-anchoring device differs from the first embodiment in the design of the receiving part body and the locking ring. The receiving part body 5' does not have the recess 30 at the second end 9b. Instead of this, the receiving part body 5' has two notch-like recesses 40 near the open end 17 of the head receiving portion 16 and an annular recess 41 adjacent to the open end 17 of the head receiving portion 16. The notch-like recesses 40 are located diametrically opposite to each other at both sides of the U-shaped recess 12 of the rod receiving portion 9. They are arranged at a distance from the open end 17. The cross-section of the notch-like recesses 40 can be V-shaped, preferably with an angle of 45° formed by the two sidewalls of the notch-like recess. Here, as can be best seen in FIG. 22b to FIG. 24b, a downwardly inclined surface 40a is formed. By the inclined surface 40a and the recess 41, a projection 42 is formed which cooperates with a flexible portion of the locking ring as described below. The number of recesses 40 is not limited to two. A larger or smaller number of recesses can also be provided. The recesses are located preferably at locations of the head receiving portion 16 between slits 19.

The locking ring 80 differs from the locking ring 8 in that the third portion 83' formed by the annular rim does not have slits so that it is not flexible. Furthermore, the inner surface portion 81a' of the first portion 81 is not tapered, but inwardly curved, as shown in FIGS. 20 to 24. However, the inner surface portion 81a' can also be tapered.

In the first portion 81 of the locking ring 80, two inwardly directed resilient noses 90 are formed which are located diametrically opposite to each other and on both sides of the projections 21 at positions where they can engage the notch-like recesses 40 of the head receiving portion 16. Between the noses and the outer surface, a hollow portion 91 is provided which allows the noses 90 to resiliently deflect. The dimension of each nose is such that it can engage the notch-like recess 40.

The function of the bone-anchoring device according to the second embodiment is now described with respect to FIGS. 22a to 24b. In the first position $P_1$, which is the insertion position, the locking ring abuts with its annular surface 82a against the second end 9b of the rod receiving portion 9 as shown in FIGS. 22a and 22b. In this position, the nose 90 engages the notch-like recess 40. The locking ring 80 is held in this position by the pre-stress exerted by the resilient nose 90. In this position, the head 3 can be inserted from the open end 17.

As shown in FIGS. 23a and 23b, the second position $P_2$ is the pre-locking position, which is defined in such a way that the nose 90 engages the annular recess 41 adjacent the open end 17. This position is achieved by shifting the locking ring 80 downward. The nose 90 is guided by the inclined surface 40a until it snaps behind the projection 42. Achieving the pre-locking position $P_2$ is thus facilitated. Here, the angle of the sidewalls of the notch-like recess are approximately 45°. The locking ring 80 can be released from the pre-locking position by the application of an instrument or manually, whereby the nose 90 is released from engagement with the annular recess 41.

As shown in FIGS. 24a and 24b a further downward movement of the locking ring 80 by tightening the inner screw which presses onto the rod 6 brings the locking ring 80 into a third position $P_3$, which is the locking position. In the locking position, the nose is shifted out of the recess 41 so that it is located beneath the open end. In this position the interior surface portion 81a' of the locking ring 80 compresses the head receiving portion 16 so that the head 3 is locked.

It should be noted that the rim 83' in this embodiment can be omitted.

The clinical use of the bone-anchoring device is similar to that of the first embodiment.

Figure 25:
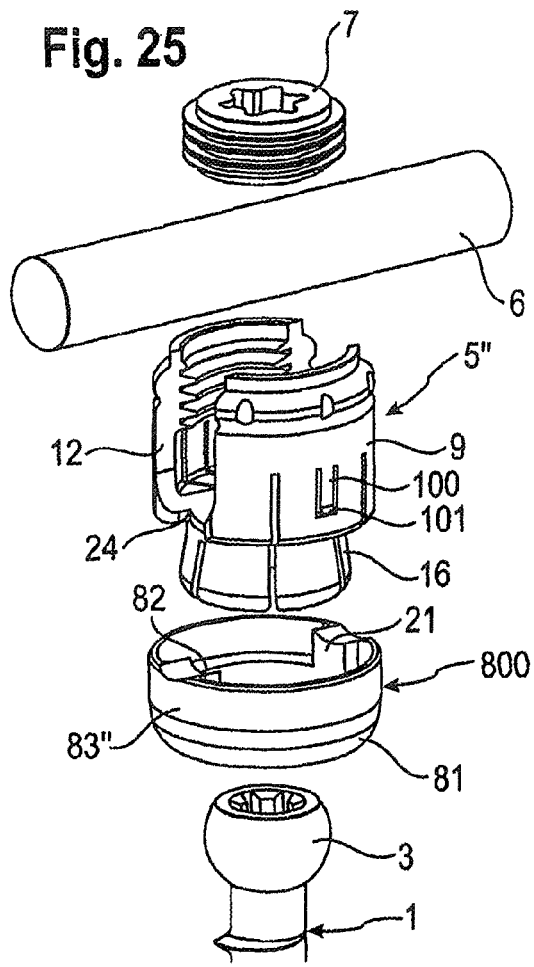
FIG. 25 shows a perspective exploded view of a third embodiment of the bone anchoring device.
Figure 26:
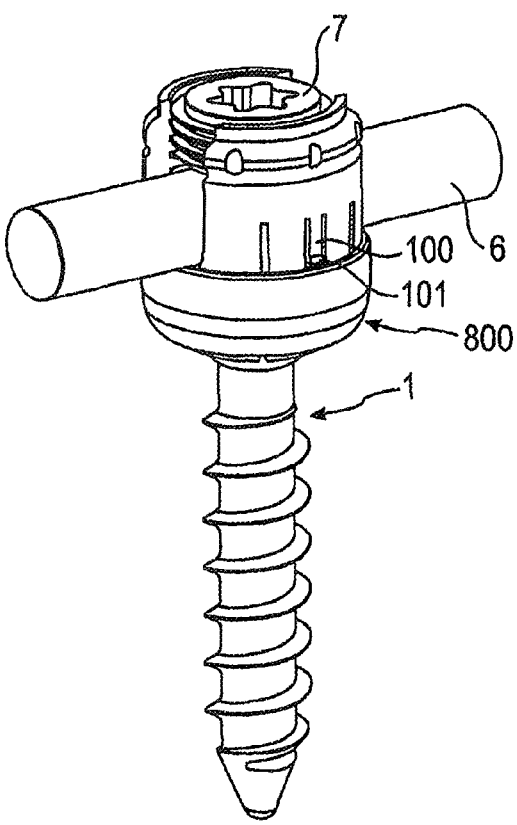
FIG. 26 shows a perspective view of the bone anchoring device of FIG. 25 in an assembled state.
Figure 27:
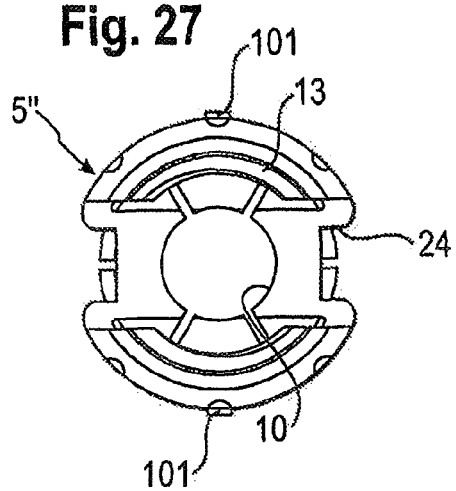
FIG. 27 shows a top view of the receiving part body of the third embodiment.

A third embodiment of the bone anchoring device is now described with respect to FIGS. 25 to 30. Parts which are similar to those of the first embodiment have the same reference numerals and the descriptions thereof will not be repeated. The third embodiment of the bone-anchoring device differs from the first embodiment in the design of the receiving part body and the locking ring. The receiving part 5" has a spring portion in its outer wall which cooperates with the locking ring 800. The spring portion is formed by a coaxially extending longitudinal element 100 arranged diametrically opposite at the outer wall of the rod receiving portion, for example on the legs 12a, 12b. The element 100 is a leaf spring-like part with a bent outward portion 101 which is formed in the outer wall of the rod receiving portion. The bent outward portion 101 projects from the wall and can be resiliently pressed into a corresponding cavity in the wall.

The locking ring 800 differs from the locking ring 8 of the first embodiment in that the rim 83" is not flexible.

In the first position, as shown in FIG. 28, the locking ring 800 is held by the pre-stress exerted by the spring portion 100 onto the rim 83". The head receiving portion is not compressed which allows introduction of the head 3. In the second, pre-locked position shown in FIG. 29, the locking ring is released from the spring element 100 and shifted downward. The spring element may act as a stop defining the pre-locking position. In the third position shown in FIG. 30, the locking ring 800 is further shifted downward and the head is locked.

In other embodiments, other shapes and numbers of the spring portion are also possible.

Further modifications of the embodiments shown are possible. For example, the head of the bone anchoring element can have any other shape, such as, for example, a cylindrical shape, whereby a monoaxial bone screw is provided allowing rotation of the screw element with respect to the receiving part around a single axis. The head 3 can also be conically shaped or otherwise shaped, where the internal hollow section 18 of the head receiving portion is adapted to this shape. In a further modification, the receiving part body 5 or at least the head receiving portion 16 may be made of bio-compatible plastic material or similar material which provides elasticity to a certain degree. In this case, the slits may be omitted.

In some embodiments, the projections of the locking ring which engage the rod can have various other shapes. For example, the surface of the free end can be flat or be otherwise shaped. The projections can be omitted.

In some embodiments, the head receiving portion can have an inclined open end 17 to allow greater angulation of the head in one direction.

In some embodiments, the outer surface of the head receiving portion can be spherical, while the inner surface of the locking ring can be tapered.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A receiving part for receiving a rod for coupling the rod to a bone anchoring element, the receiving part comprising:
   a receiving part body comprising:
     a rod receiving portion having a channel for receiving a rod, and
     a head receiving portion for accommodating a head of a bone anchoring element, the head receiving portion having an open end and being flexible for inserting and clamping of the head; and
   a locking ring configured to be positioned around the head receiving portion, wherein when the locking ring is around the head receiving portion, an abutment between the locking ring and the receiving part body restricts rotation of the locking ring around the receiving part body,
   wherein in a pre-locking position of the locking ring, a spring portion on one of the locking ring or the receiving part body engages a corresponding portion on the other one of the locking ring or the receiving part body to restrict the locking ring from moving away from the open end of the head receiving portion of the receiving part body, and the locking ring restricts expansion of the head receiving portion,
   wherein in a locking position of the locking ring, the locking ring exerts a force onto the head receiving portion to lock the head therein.

2. The receiving part of claim 1, wherein the spring portion is provided at an edge of the locking ring.

3. The receiving part of claim 1, wherein the locking ring has a lower edge facing the open end of the head receiving portion and an upper edge facing away from the open end, and wherein the spring portion is arranged at the upper edge of the locking ring.

4. The receiving part of claim 3, wherein the spring portion is formed by a radially flexible upper rim.

5. The receiving part of claim 4, wherein the spring portion is fanned by at least one coaxial slit in the upper rim.

6. The receiving part of claim 3, wherein the spring portion is configured to engage a recess in the rod receiving portion or an end of the rod receiving portion.

7. The receiving part of claim 1, wherein the locking ring has a lower edge facing the open end of the head receiving portion and an upper edge facing away from the open end, and wherein the spring portion is arranged at the lower edge of the locking ring.

8. The receiving part of claim 7, wherein the spring portion is formed by at least one radially flexible projection.

9. The receiving part of claim 8, wherein the at least one projection comprises at least two radially flexible noses.

10. The receiving part of claim 8, wherein the at least one projection is configured to engage a recess in the head receiving portion.

11. The receiving part of claim 10, wherein the recess is arranged near the open end of the head receiving portion.

12. The receiving part of claim 10, wherein the recess has a notch-like shape and comprises a downward inclined side wall for facilitating release of the flexible projection to move the locking ring from the pre-locking position.

13. The receiving part of claim 1, wherein the head receiving portion has an exterior surface with a tapered portion and the locking ring has an interior surface with a tapered portion or a curved portion having a convex curvature.

14. The receiving part of claim 1, wherein the locking ring is configured to move upon exerting a pressure onto the locking ring via the rod.

15. The receiving part of claim 1, wherein the rod receiving portion comprises a first end and a second end, and a recess extends from the first end in the direction of the second end to form the channel.

16. The receiving part of claim 1, wherein the rod receiving portion has a first end and a second end, and the head receiving portion is arranged at the second end, and wherein an outer diameter of the head receiving portion adjacent to the second end is smaller than an outer diameter of the second end of the rod receiving portion.

17. The receiving part of claim 1, wherein the receiving part body comprises a plurality of slits adjacent to the open end.

18. The receiving part of claim 17, wherein at least one of the plurality of slits extends continuously from the open end of the head receiving portion into the rod receiving portion.

19. The receiving part of claim 1, wherein the spring portion is on the receiving part body.

20. A bone anchoring device comprising:
   a bone anchoring element having a threaded shaft and a head; and
   a receiving part for receiving a rod for coupling the rod to the bone anchoring element, the receiving part comprising:
     a receiving part body comprising a rod receiving portion having a channel for receiving the rod, and a head receiving portion for accommodating the head of the bone anchoring element, the head receiving portion having an open end and being flexible for inserting and clamping of the head; and
     a locking ring configured to be positioned around the head receiving portion, wherein when the locking ring is around the head receiving portion, an abutment between the locking ring and the receiving part body restricts rotation of the locking ring around the receiving part body,
   wherein in a pre-locking position of the locking ring, a spring portion on one of the locking ring or the receiving part body engages a corresponding portion on the other one of the locking ring or the receiving part body to restrict the locking ring from moving away from the open end of the head receiving portion of the receiving part body, and the locking ring restricts expansion of the head receiving portion to hold the head of the bone anchoring element in the receiving part body,
   wherein in a locking position of the locking ring, the locking ring exerts a force onto the head via the head receiving portion to lock an angular position of the bone anchoring element relative to the receiving part body.

21. The bone anchoring device of claim 20, further comprising:
- the rod; and
- a closure element for securing the rod in the channel.

22. A method of coupling a rod to a bone anchoring element via a receiving part, the receiving part comprising a receiving part body comprising a rod receiving portion having a channel for receiving the rod and a head receiving portion having an open end and being flexible for inserting and clamping of a head of the bone anchoring element, and a locking ring around the head receiving portion of the receiving part body, wherein an abutment restricts rotation of the locking ring around the receiving part body, the method comprising:
- introducing the head of the bone anchoring element into the open end of the head receiving portion;
- advancing the locking ring relative to the head receiving portion until a spring portion on one of the locking ring or the receiving part body engages a corresponding portion on the other one of the locking ring or the receiving part body to restrict the locking ring from moving away from the open end of the head receiving portion of the receiving part body, where the locking ring restricts expansion of the head receiving portion to hold the head of the bone anchoring element in the receiving part body;
- pivoting the receiving part relative to the bone anchoring element to align the receiving part with the rod;
- inserting the rod into the channel of the rod receiving portion;
- advancing a closure element in the channel to push the rod against the looking ring; and
- further advancing the closure element in the channel toward the head receiving portion to further advance the locking ring relative to the head receiving portion to a locking position via the rod, where the locking ring exerts a force on the head via the head receiving portion to lock an angular position of the bone anchoring element relative to the receiving part body.

* * * * *

UNITED STATES PATENT AND TRADEMARK OFFICE
CERTIFICATE OF CORRECTION

PATENT NO.        : 9,023,086 B2  
APPLICATION NO.   : 13/942418  
DATED             : May 5, 2015  
INVENTOR(S)       : Lutz Biedermann et al.

Page 1 of 1

It is certified that error appears in the above-identified patent and that said Letters Patent is hereby corrected as shown below:

In the Claims

Column 9, Claim 5, line 57          Delete "fanned"  
                                    Insert -- formed --

Column 10, Claim 20, line 50        Delete "looking"  
                                    Insert -- locking --

Column 12, Claim 22, line 12        Delete "looking"  
                                    Insert -- locking --

Signed and Sealed this  
Twenty-third Day of February, 2016

Michelle K. Lee  
*Director of the United States Patent and Trademark Office*